United States Patent
Razzetti et al.

(10) Patent No.: US 7,345,072 B2
(45) Date of Patent: Mar. 18, 2008

(54) PHENYLTETRAZOLE COMPOUNDS

(75) Inventors: Gabriele Razzetti, Sesto S. Giovanni (IT); Domenico Magrone, Milan (IT); Mauro Ercoli, Milan (IT)

(73) Assignee: Dipharma S.p.A., Mereto di Tomba (IT)

( * ) Notice: Subject to any disclaimer, the term of this patent is extended or adjusted under 35 U.S.C. 154(b) by 560 days.

(21) Appl. No.: 10/995,135

(22) Filed: Nov. 24, 2004

(65) Prior Publication Data
US 2005/0119488 A1 Jun. 2, 2005

(30) Foreign Application Priority Data
Nov. 28, 2003 (IT) .......................... MI2003A2338

(51) Int. Cl.
*A61K 31/41* (2006.01)
*C07D 257/04* (2006.01)

(52) U.S. Cl. ...................... 514/381; 514/385; 548/250; 548/300.1

(58) Field of Classification Search ................ 514/381, 514/385; 548/250, 300.1
See application file for complete search history.

(56) References Cited

U.S. PATENT DOCUMENTS 6,264,914 B1 * 7/2001 Klaveness et al. ......... 424/1.65

* cited by examiner

*Primary Examiner*—Rebecca Anderson
*Assistant Examiner*—Susannah Chung
(74) *Attorney, Agent, or Firm*—Young & Thompson

(57) ABSTRACT

Novel phenyltetrazole compounds useful as intermediates in the preparation of angiotensin II antagonists and the processes for the conversion thereof to biologically active molecules.

17 Claims, No Drawings

PHENYLTETRAZOLE COMPOUNDS

FIELD OF THE INVENTION

The present invention relates to novel substituted phenyltetrazole compounds useful as intermediates in the preparation of angiotensin II antagonists, and a process for the conversion thereof to said molecules.

TECHNOLOGICAL BACKGROUND

Angiotensin II antagonists are medicaments useful in the treatment of hypertension, anxiety, glaucoma and cardiac attacks. A number of these compounds share a biphenyltetrazole moiety and can be represented by the following formula (I)

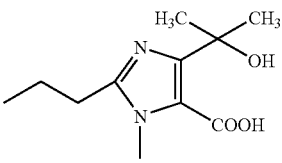

wherein Z is an optionally substituted heterocycle containing at least one nitrogen atom; or an open amide residue.

More particularly, the substituent Z can have the following meanings (a)

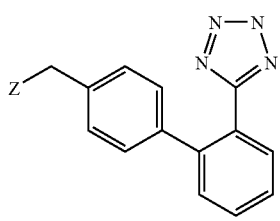

(b)

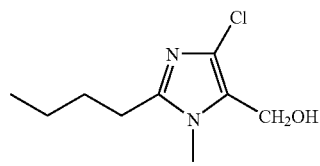

(c)

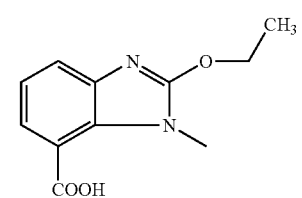

(d)

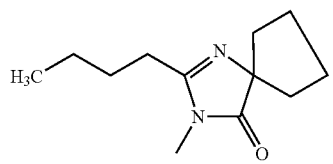

(e)

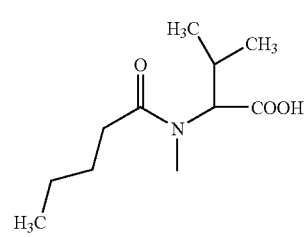

which identify specific angiotensin II antagonists: (a) [2-butyl-4-chloro-5-hydroxymethyl-imidazol-1-yl] losartan; (b) [2-ethoxy-3H-benzimidazole-4-carboxylic acid] candesartan; (c) [2-butyl-1,3-diaza-spiro[4,4]non-1-en-4-on-3-yl] irbesartan; (d) [(S)—N-(1-carboxy-2-methylprop-1-yl)-N-pentanoylamino] valsartan; and (e) [5-carboxy-4-(1-hydroxy-1-methylethyl)-2-propy-imidazo-1-yl] olmesartan.

A number of processes for the preparation of the compounds of formula (I) are known. For example, according to EP 253310, losartan can be prepared by reaction between a compound of formula (III)

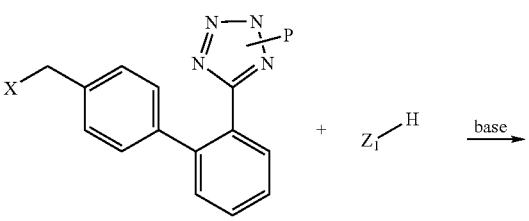

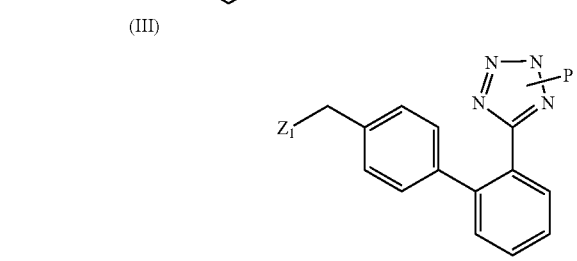

wherein X is a leaving group and P is a tetrazole protecting group, and a base $Z_1$-H, wherein $Z_1$ has the meaning as indicated in (a); the subsequent removal of the protecting group P affords losartan.

WO93/10106 discloses the preparation of losartan by cross coupling reaction between a compound of formula (IV)

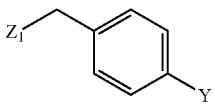

wherein $Z_1$ has the meaning as indicated in (a) above, Y is a leaving group such as halogen, methanesulfonyloxy, fluorosulfonyloxy or trifluoromethanesulfonyloxy; and a synthon of formula (V)

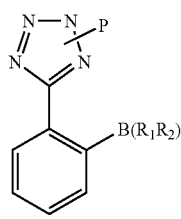

(V)

wherein —B(R₁R₂) is a disubstituted boron atom and P is a tetrazole protecting group, to obtain the compound of formula (II) reported above, and subsequent removal of the protecting group P.

Candesartan, irbesartan, valsartan, and olmesartan can be obtained analogously.

Generally speaking, a protecting group is a group which blocks a reactive site in a compound having more than one reactive group, so that the chemical reaction can be carried out selectively on another unprotected reactive site, said protecting group being easily removed at the end of the selective reaction.

The compounds of formula (II), (III) and (V) reported above contain a tetrazol-5-yl group, in which a reactive nitrogen atom is present. It is known that the reactive tetrazole nitrogen in a compound of formula (II), (III) and (V) can be protected with a group such as triphenylmethyl, p-nitrophenyl, pyridyl or pyrimidyl. Analogously, the 1-methyl-1-phenylethyl group would be a very good protecting group for the reactive tetrazole nitrogen, in that it is particularly resistant to cleavage during the selective reaction, but it also is resistant to cleavage after completion of the reaction.

U.S. Pat. No. 5,412,102 discloses the use of the 1-methyl-1-phenylethyl group (cumyl) as a protecting group in the preparation of 1-butyl-2-[2'-(2H-tetrazol-5-yl)biphenyl-4-yl-methyl]-1H-indole-3-carboxylic acid. The deprotection is carried out by reaction with about 3-4 equivalents of a Lewis acid, preferably boron trifluoride etherate (see example 15), in the presence of a thiol, an arylthiol, a 2-mercaptoacetic acid, preferably a 2-mercaptoacetate, or pentaerythritol tetrakis(2-mercaptoacetate).

The removal of the cumyl protecting group is efficient, but the reagents used do not fulfil the requirements for the production on an industrial scale. Boron trifluoride etherate is in fact a dangerous, flammable compound (Bretherick, Handbook of reactive chemical hazards, IV ed. page 481). Similarly, thiols and the derivatives thereof are remarkably difficult to use. There is therefore the need for of a novel process which allows to remove the 1-methyl-1-phenylethyl group from the phenyltetrazole derivatives, overcoming the mentioned problems.

SUMMARY OF THE INVENTION

An efficient method for removing the reactive tetrazole nitrogen 1-methyl-1-phenylethyl protecting group has been found. Said method is particularly useful in the preparation of losartan, valsartan, irbesartan, candesartan, and olmesartan, using the novel intermediates thereof in which the reactive tetrazole nitrogen is protected by said 1-methyl-1-phenylethyl group.

DETAILED DISCLOSURE OF THE INVENTION

A first aspect of the invention is a process for deprotecting the reactive tetrazole nitrogen in a compound containing a 2-(1-methyl-1-phenylethyl)-2H-tetrazolyl group, comprising the reaction of said protected compound with an anhydrous hydrohalic acid or with an aqueous solution thereof at a concentration higher than 20% weight/weight.

A compound containing a 2-(1-methyl-1-phenylethyl)-2H-tetrazolyl group is preferably a compound of formula (VI)

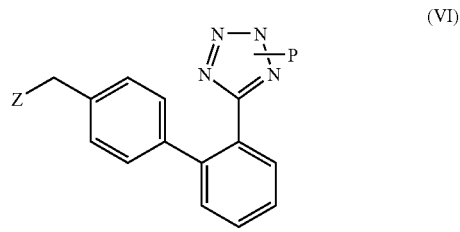

(VI)

wherein P is a 1-methyl-1-phenylethyl group; and Z has one of the following meanings (a), (b), (c), (d), or (e)

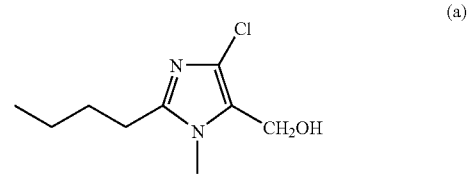

(a)

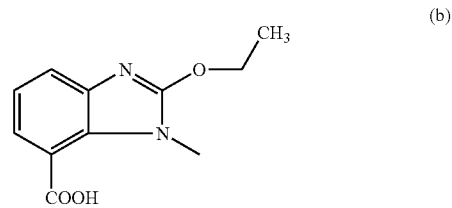

(b)

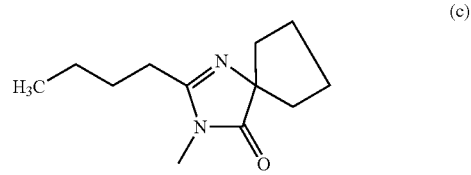

(c)

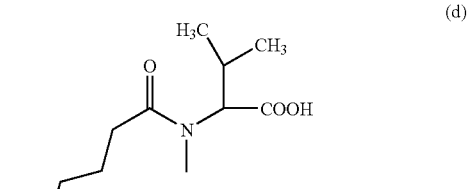

(d)

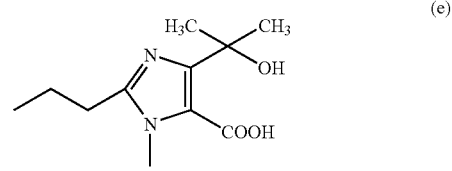

(e)

A hydrohalic acid preferably is an acid selected from the group consisting of hydrochloric acid and hydrobromic acid.

When the hydrohalic acid is used in the anhydrous form (gas), the reaction can be carried out in an organic protic or aprotic solvent.

An organic protic solvent may be a $C_1$-$C_4$ alkanol, such as methanol, ethanol, isopropanol or butanol. An organic aprotic solvent may be an ether, such as tetrahydrofuran or dioxane; an ester, such as ethyl acetate, butyl acetate or isopropyl acetate; a hydrocarbon, such as toluene; a chlorinated solvent, such as dichloromethane, dichloroethane or chlorobenzene; a keton, such as acetone; or a nitrile, such as acetonitrile.

Hydrochloric acid is typically used in aqueous solution or as a gas (anhydrous) in an organic protic or aprotic solvent; hydrobromic acid is typically used in aqueous solution.

The reaction is preferably carried out using hydrochloric acid in aqueous solution at a concentration equal to or higher than 30% w/w, more preferably equal to or higher than 35%, or anhydrous hydrochloric acid (gas) in dichloromethane or ethyl acetate solution.

Hydrobromic acid is typically used at a concentration equal to or higher than 35% w/w, preferably equal to or higher than 40%.

The amount of hydrohalic acid used ranges from 1.1 moles to 5 moles, compared with the substrate to be deprotected, preferably from 2 to 3 moles.

The reaction can be carried out at a temperature ranging from 0° C. to the reflux temperature of the solvent mixture, preferably from 15° C. to 70° C.

When the reaction is carried out with a hydrohalic acid aqueous solution, an organic protic or aprotic solvent, as defined above, preferably toluene, in homogeneous or heterogeneous mixture with water, can be used as co-solvent.

A further aspect of the invention is a process for the preparation of losartan, valsartan, irbesartan, candesartan, and olmesartan comprising the removal of the 1-methyl-1-phenylethyl protecting group in a compound of formula (VI),

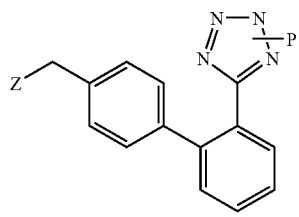

(VI)

wherein P is a 1-methyl-1-phenylethyl group; and Z has the following meanings

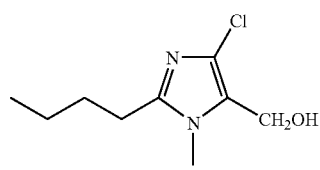

(a)

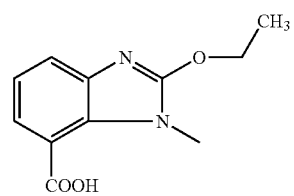

(b)

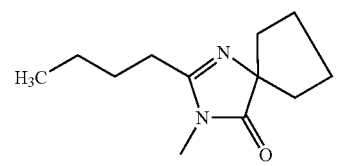

(c)

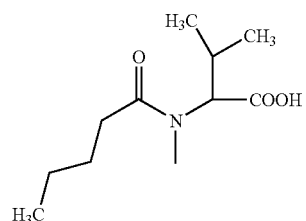

(d)

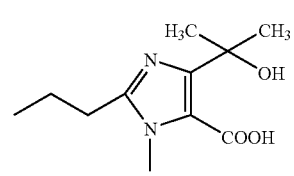

(e)

by reacting a compound of formula (VI) with an anhydrous hydrohalic acid or an aqueous solution thereof at a concentration above 20% w/w.

The compounds of formula (VI) reported above, as well as the isomers and tautomers thereof, are novel compounds and are a further object of the invention. They can be prepared according to the procedures mentioned in EP 253310 and WO 93/10106. In particular, the reactive tetrazole nitrogen can be protected with a 1-methyl-1-phenylethyl group as described in example 2 of U.S. Pat. No. 5,412,102.

The following examples illustrate the invention.

EXAMPLE 1

Preparation of (2-butyl-5-chloro-3-{2'-[2-(1-methyl-1-phenyl-ethyl)-2H-tetrazol-5-yl]-biphenyl-4-ylmethyl}-3H-imidazol-4-yl)-methanol; [(VI), Z is 2-butyl-4-chloro-5-hydroxymethyl-imidazol-1-yl; P is 1-methyl-1-phenylethyl (cumyl)]

A suspension of [2'-(1-methyl-1-phenyl-ethyl)]-2H-tetrazol-5-yl]phenyl boronic acid (26.7 mmoles, 8.3 g) in diethoxymethane is added under stirring with two portions of water (0.55 ml, 31 mmoles) at room temperature, in about 1 hour. After completion of the addition, potassium carbonate (8.6 g, 62 mmoles), [3-(4-bromo-benzyl)-2-butyl-5-chloro-3H-imidazol-4-yl]-methanol (8.97 g, 25 mmoles), triphenylphosphine (262 mg, 1.0 mmoles), palladium acetate (56 mg, 0.25 mmoles) and THF (20 ml) are added. The mixture is refluxed for 6 hours, then the aqueous phase is discarded. The organic phase is washed with 30 ml of water, concentrated to dryness and the resulting product is crystallized from isopropanol, thereby obtaining 10.6 g of (2-butyl-5-chloro-3-{2'-[2-(1-methyl-1-phenyl-ethyl)-2H-tetrazol-5-yl]-biphenyl-4-ylmethyl}-3H-imidazol-4-yl)-methanol.

NMR: ($^1$H, DMSO, 300 mHz): δ 0.79 (3H, t, J=8, CH$_3$), 1.20 (2H, sext, J=8, CH$_3$CH$_2$), 1.42 (2H, quin, J=8, CH$_3$CH$_2$CH$_2$), 1.91 (6H, s, CMe$_2$), 2.41 (2H, t, J=8, CH$_3$CH$_2$CH$_2$CH$_2$), 4.30 (2H, d, J=3, CH$_2$OH), 5.15-5.20 (3H, m, CH$_2$Ar and OH), 6.88-7.0 (4H, m, ArH), 7.08 (2H, d, J=8, ArH), 7.22-7.29 (3H, m, ArH), 7.41-7.62 (3H, m, ArH), 7.88 (1H, d, J=7, ArH). ($^{13}$C, DMSO, 300 mHz): δ 14.3, 22.32, 26.5, 29.2, 29.6, 47.1, 52.1, 68.8, 125.1, 126.0, 126.3, 126.5, 126.7, 128.3, 128.5, 129.2, 129.9, 130.1, 131.0, 131.2, 136.4, 140.1, 141.7, 144.6, 147.9, 164.6.

The following compounds can be prepared analogously:
2-butyl-3-{2'-[2-(1-methyl-1-phenyl-ethyl)-2H-tetrazol-5-yl]-biphenyl-4-ylmethyl}-1,3-diaza-spiro[4.4]non-1-en-4-one;
(S)—N-(1-oxopentyl)-N-[[2'-[(1-methyl-1-phenyl-ethyl)-2H-tetrazol-5-yl][1,1'-biphenyl]-4-yl]methyl]-valine;
2-ethoxy-3-{2'-[2-(1-methyl-1-phenyl-ethyl)-2H-tetrazol-5-yl]-biphenyl-4-ylmethyl}-3H-benzoimidazole-4-carboxylic acid; and
(1H-imidazole-5-carboxylic acid, 4-(1-hydroxy-1-methylethyl)-2-propyl-1-[[2'-[2-(1-methyl-1-fenylethyl)-1H-tetrazol-5-yl)[1,1'-biphenyl]-4-yl]methyl)

EXAMPLE 2

Removal of the Protecting Group from a Compound (VI)

10 g (0.02 moles) of (2-butyl-5-chloro-3-{2'-[2-(1-methyl-1-phenyl-ethyl)-2H-tetrazol-5-yl]-biphenyl-4-ylmethyl}-3H-imidazol-4-yl)-methanol are dissolved in 50 ml of 37% aqueous hydrochloric acid under stirring at a temperature of 15-20° C. The mixture is stirred for a further 4 h, then washed 3 times with 25 ml of toluene. The aqueous phase is poured into a solution of 55 g of sodium acetate in water, the formed precipitate is filtered, thoroughly washed with water and dried under vacuum at 70° C., thereby obtaining 8 g of losartan.

NMR: 1H (DMSO, 300 mHz): δ 0.80 (3H, t, J=10, CH3), 1.25 (2H, sest, J=10, CH3CH2), 1.45 (2H, quin, J=10, CH3CH2CH2), 2.45-2.55 (2H, m, CH3CH2CH2CH2), 4.30 (2H, 2H, CH2OH), 5.30 (2H, s, CH2Ar), 7.10 (4H, s, ArH), 7.45-7.70 (4H, m, ArH).

Operating analogously, from the respective intermediates of formula (VI) obtainable according to Example 1, the following compounds: valsartan, irbesartan, candesartan and olmesartan can be obtained.

EXAMPLE 3

Removal of the Protecting Group from a Compound (VI)

10 g (0.02 moles) of (2-butyl-5-chloro-3-{2'-[2-(1-methyl-1-phenyl-ethyl)-2H-tetrazol-5-yl]-biphenyl-4-ylmethyl}-3H-imidazol-4-yl)-methanol are dissolved in 50 ml of dichloromethane and gaseous HCl is bubbled at a temperature of 0-10° C. After 2 h the reaction mixture is poured into a solution of 55 g of sodium acetate in water, the formed precipitate is filtered, thoroughly washed with water and dried under vacuum at 70° C., thereby obtaining 7.8 g of losartan.

Operating analogously, from the respective intermediates of formula (VI) obtainable according to Example 1, the following compounds: valsartan, irbesartan, candesartan and olmesartan can be obtained.

EXAMPLE 4

Removal of the Protecting Group from a Compound (VI)

10 g (0.02 moles) of (2-butyl-5-chloro-3-{2'-[2-(1-methyl-1-phenyl-ethyl)-2H-tetrazol-5-yl]-biphenyl-4-ylmethyl}-3H-imidazol-4-yl)-methanol are dissolved in 50 ml of 40% aqueous hydrobromic acid under stirring at a temperature of 15-20° C. The mixture is stirred for a further 4 h, then washed 3 times with 25 ml of toluene. The aqueous phase is poured into a solution of 55 g of sodium acetate in water, the formed precipitate is filtered, thoroughly washed with water and dried under vacuum at 70° C., thereby obtaining 7.8 g of losartan.

Operating analogously, from the respective intermediates of formula (VI) obtainable according to Example 1, the following compounds: valsartan, irbesartan, candesartan and olmesartan can be obtained.

EXAMPLE 5

Removal of the Protecting Group from a Compound (VI)

124 g (0.228 moles) of 2-butyl-3-{2'-[2-(1-methyl-1-phenyl-ethyl)-2H-tetrazol-5-yl]-biphenyl-4-ylmethyl}-1,3-diaza-spiro[4.4]non-1-en-4-one are dissolved in 500 ml of toluene and 900 ml of 37% aqueous hydrochloric acid are added thereto under stirring at a temperature of 15-20° C. The mixture is stirred for a further 4 h, then the aqueous phase is separated and washed twice with 250 ml of toluene. The aqueous phase is poured into a solution of 125 g of sodium acetate in water, the formed precipitate is filtered, thoroughly washed with water and dried under vacuum at 70° C., thereby obtaining 77 g of irbesartan.

NMR: $^1$H (DMSO, 300 mHz): δ 0.80 (3H, t,); 1.26-(2H, m), 1.46 (2H, m); 1.65-1.84 (8H, m); 2.29 (2H, t); 4.67 (2H, s); 7.08 (4H,s); 7.60 (4H, m).

Operating analogously, from the respective intermediates of formula (VI) obtainable according to Example 1, the following compounds: valsartan, losartan, candesartan and olmesartan can be obtained.

The invention claimed is:

1. A process for the deprotection of the reactive tetrazole nitrogen in a compound containing a 2-(1-methyl-1-phenylethyl)-2H-tetrazolyl group, comprising the reaction of the protected compound with an anhydrous hydrohalic acid or an aqueous solution thereof at a concentration higher than 20% w/w.

2. The process according to claim 1, wherein the acid is selected from the group consisting of hydrochloric acid and hydrobromic acid.

3. The process according to claim 2, wherein the amount of acid used ranges from 1.1 moles to 5 moles, compared with the substrate to be deprotected.

4. The process according to claim 2, wherein the hydrochloric acid aqueous solution has concentration equal to or higher than 30% w/w.

5. The process according to claim 2, wherein the hydrobromic acid aqueous solution has concentration equal to or higher than 35% w/w.

6. The process according to claim 1, wherein the reaction is carried out with an anhydrous hydrohalogen acid in an organic protic or aprotic solvent.

7. The process according to claim 6, wherein the solvent is selected from a $C_1$-$C_4$ alkanol; an ether; an ester; a hydrocarbon; a chlorinated solvent; a keton or a nitrile.

8. The process according to claim 7, wherein the reaction is carried out in dichloromethane or ethyl acetate.

9. The process according to claim 1, wherein an organic protic or aprotic solvent, in homogeneous or heterogeneous mixture with water, is used as co-solvent.

10. The process according to claim 9, wherein said solvent is toluene.

11. The process according to claim 1, wherein said compound is a compound of formula (VI),

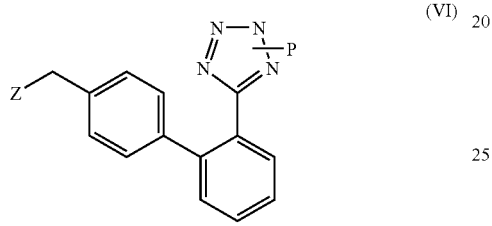

(VI)

wherein P is a 1-methyl-1-phenylethyl group; and Z has the following meanings

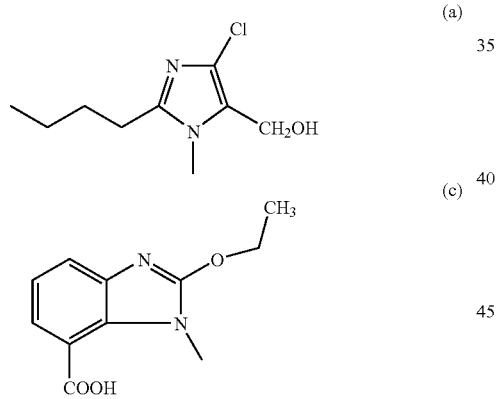

(a)

(c)

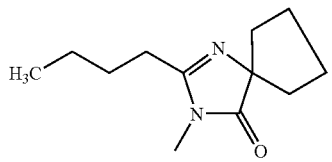

(b)

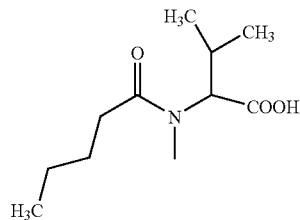

(d)

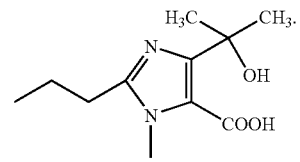

(e)

12. The process according to claim 3, wherein the hydrochloric acid aqueous solution has concentration equal to or higher than 30% w/w.

13. The process according to claim 3, wherein the hydrobromic acid aqueous solution has concentration equal to or higher than 35% w/w.

14. The process according to claim 2, wherein the reaction is carried out with an anhydrous hydrohalogen acid in an organic protic or aprotic solvent.

15. The process according to claim 3, wherein the reaction is carried out with an anhydrous hydrohalogen acid in an organic protic or aprotic solvent.

16. The process according to claim 4, wherein an organic protic or aprotic solvent, in homogeneous or heterogeneous mixture with water, is used as co-solvent.

17. The process according to claim 5, wherein an organic protic or aprotic solvent, in homogeneous or heterogeneous mixture with water, is used as co-solvent.

* * * * *